United States Patent
Olds et al.

(10) Patent No.: US 9,802,060 B2
(45) Date of Patent: *Oct. 31, 2017

(54) LIGHT THERAPY MONITORING

(71) Applicant: SunSprite, Cambridge, MA (US)

(72) Inventors: Jacqueline Olds, Cambridge, MA (US); Richard S. Schwartz, Cambridge, MA (US); Thomas C. Hayes, Cambridge, MA (US); Kasey J. Russell, Windham, NH (US)

(73) Assignee: SunSprite, Cambridge, MA (US)

( * ) Notice: Subject to any disclaimer, the term of this patent is extended or adjusted under 35 U.S.C. 154(b) by 148 days.

This patent is subject to a terminal disclaimer.

(21) Appl. No.: 14/864,525

(22) Filed: Sep. 24, 2015

(65) Prior Publication Data

US 2016/0016005 A1      Jan. 21, 2016

Related U.S. Application Data

(63) Continuation of application No. 13/939,217, filed on Jul. 11, 2013, now Pat. No. 9,163,983, which is a
(Continued)

(51) Int. Cl.
*A61N 5/06* (2006.01)
*G01J 1/44* (2006.01)
(Continued)

(52) U.S. Cl.
CPC .............. *A61N 5/0618* (2013.01); *G01J 1/44* (2013.01); *H05B 37/0218* (2013.01);
(Continued)

(58) Field of Classification Search
CPC ........ A61B 5/02438; A61N 2005/0628; A61N 2005/0645; A61N 5/0618; G01J 1/44; G01J 2001/4276; H05B 37/0218; Y02B 20/46

See application file for complete search history.

(56) References Cited

U.S. PATENT DOCUMENTS

| | | |
|---|---|---|
| 3,268,839 A | 8/1966 | McFarland |
| 3,878,496 A | 4/1975 | Erickson |

(Continued)

FOREIGN PATENT DOCUMENTS

| | | |
|---|---|---|
| WO | 01/52736 A1 | 7/2001 |
| WO | 2005/103923 A2 | 11/2005 |

(Continued)

OTHER PUBLICATIONS

Chandra, et al., "Treatment of vitamin D deficiency with UV light in patients with malabsorption syndromes: a case series", 23 Photodermatol. Photoimmunol. Photomed. 179-185 (Oct. 2007).

(Continued)

*Primary Examiner* — Francis M Legasse, Jr.
(74) *Attorney, Agent, or Firm* — Modern Times Legal; Robert J. Sayre

(57) ABSTRACT

A light-monitoring apparatus includes a power source, a light detector, a computer processor coupled with the power source and in communication with the light detector and configured to receive and record light exposure detected by the light detector, an output device coupled with the computer processor, and a computer-readable medium coupled with the computer processor and storing instruction code for summing the recorded light exposure from the computer processor over time and communicating a signal to the output device to generate and communicate a signal indicating that a cumulative threshold light exposure for achieving a health benefit has been reached. The apparatus can accordingly be used by an individual to monitor cumulative light exposure from both natural and artificial sources, e.g., in the treatment of seasonal or non-seasonal depression.

18 Claims, 6 Drawing Sheets

Related U.S. Application Data continuation-in-part of application No. PCT/US2013/021150, filed on Jan. 11, 2013.

(60) Provisional application No. 61/585,907, filed on Jan. 12, 2012.

(51) Int. Cl.
  *H05B 37/02* (2006.01)
  *A61B 5/024* (2006.01)
  *G01J 1/42* (2006.01)

(52) U.S. Cl.
  CPC ... *A61B 5/02438* (2013.01); *A61N 2005/0628* (2013.01); *A61N 2005/0645* (2013.01); *G01J 2001/4276* (2013.01); *Y02B 20/46* (2013.01)

(56) References Cited

U.S. PATENT DOCUMENTS

| | | |
|---|---|---|
| 4,229,733 A | 10/1980 | Tulenko et al. |
| 4,348,664 A | 9/1982 | Boschetti et al. |
| 4,428,050 A | 1/1984 | Pellegrino et al. |
| 4,851,686 A | 7/1989 | Pearson |
| 5,008,548 A | 4/1991 | Gat |
| 5,036,311 A | 7/1991 | Moran et al. |
| 5,151,600 A | 9/1992 | Black |
| 5,365,068 A | 11/1994 | Dickerson |
| 5,500,532 A | 3/1996 | Kozicki |
| D376,547 S | 12/1996 | McRae |
| 5,992,996 A | 11/1999 | Sawyer |
| 6,322,503 B1 | 11/2001 | Sparhawk |
| 6,582,380 B2 | 6/2003 | Kazlausky et al. |
| D479,805 S | 9/2003 | Tsai |
| 7,265,358 B2 | 9/2007 | Fontaine |
| 7,808,392 B1 | 10/2010 | Anklesaria |
| 7,874,666 B2 | 1/2011 | Xu et al. |
| 8,157,730 B2 | 4/2012 | LeBoeuf et al. |
| 9,163,983 B2 | 10/2015 | Olds et al. |
| 2006/0206173 A1 | 9/2006 | Gertner et al. |
| 2008/0077199 A1 | 3/2008 | Shefi et al. |
| 2008/0265170 A1 | 10/2008 | Ales et al. |
| 2009/0090865 A1 | 4/2009 | Lub et al. |
| 2009/0318802 A1 | 12/2009 | Boyden et al. |
| 2010/0163750 A1 | 7/2010 | Hunwick et al. |
| 2010/0217099 A1* | 8/2010 | LeBoeuf .................. A61B 5/00 600/301 |
| 2011/0133103 A1 | 6/2011 | Folkesson |
| 2012/0226111 A1 | 9/2012 | LeBoeuf et al. |
| 2013/0172963 A1 | 7/2013 | Moffat |

FOREIGN PATENT DOCUMENTS

| | | |
|---|---|---|
| WO | 2011/089539 A1 | 7/2011 |
| WO | 2011/094742 A2 | 8/2011 |
| WO | 2013/106653 A1 | 7/2013 |

OTHER PUBLICATIONS

Rabin, Roni C. "A Portable Glow to Help Melt Those Winter Blues", New York Times (Nov. 14, 2011).

Rensselaer Lighting Research Center, "Dimesimeter—Light and Activity Measurement System Description and calibration" (Nov. 15, 2011).

Bharatula, Nagendra B., et al., "Towards Wearable Autonomous Microsystems", Pervasive 2004, 225-237 (2004).

NASA, "Hardware Information: Actillume", Life Sciences Data Archive, Johnson Space Center, Houston, Texas, <http://lsda.jsc.nasa.gov/cf/scripts/hardware/hw_search_start_adv.cfm> (visited Dec. 7, 2011) (Sep. 6, 2011).

US Small Business Innovation Research / Small Business Technology Transfer, "Actillume—A Monitor for Activity and Light Exposure" <http://www.sbir.gov/sbirsearch/detail/86950> (visited Dec. 7, 2011).

* cited by examiner

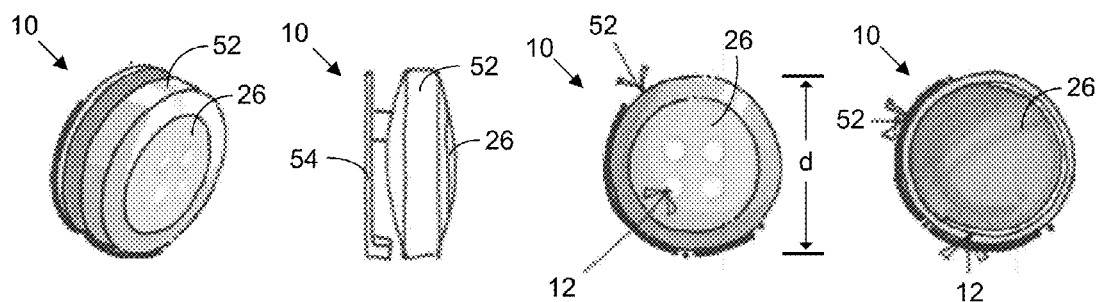
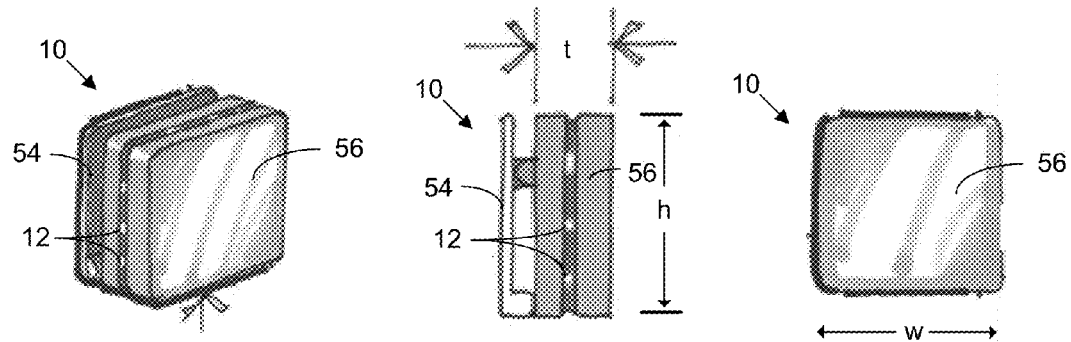
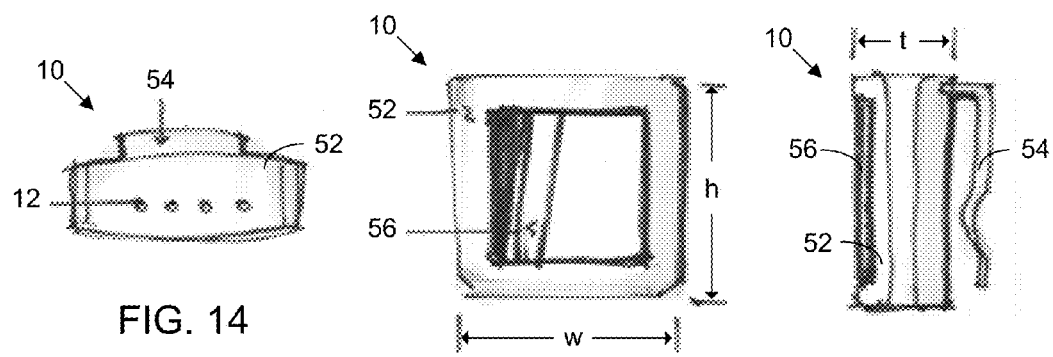

LIGHT THERAPY MONITORING

RELATED APPLICATIONS

This application is a continuation of U.S. application Ser. No. 13/939,217, filed 11 Jul. 2013, which is a continuation in part of International Application No. PCT/US2013/21150, filed on 11 Jan. 2013, the entire contents of each of which are incorporated herein by reference. This application also claims the benefit of U.S. Provisional Application No. 61/585,907, filed 12 Jan. 2012, the entire content of which is incorporated herein by reference.

BACKGROUND

Exposure to bright light has been demonstrated to be effective in multiple studies of bright-light therapy for seasonal and non-seasonal depression. These studies have also defined an optimal dose of light as a function of intensity and time. Light has an effect on hormones and neurotransmitters (e.g., melatonin and serotonin), which are involved in the regulation of mood, energy and appetite.

Studies have also demonstrated that bright light can reduce insomnia associated with circadian rhythm difficulties. Light therapy may also be helpful in treating depression during pregnancy, dementia in the elderly, bulimia nervosa, severe premenstrual syndrome, attention deficit hyperactivity disorder, and bipolar disorder.

Based on these findings, psychiatrists have conducted studies and prescribed the use of artificial light boxes, requiring patients to sit in one place, indoors, and close to the light source to provide controlled means of dosing the light to the patient. Nevertheless, and despite known benefits, bright-light therapy is not widely prescribed by doctors, according to a recent New York Times article (R. Rabin, "A Portable Glow to Help Melt Those Winter Blues," New York Times, 14 Nov. 2011).

> Why, then, do so few doctors prescribe bright-light therapy? Some say their patients don't have the patience to sit in front of a light for 30 to 45 minutes every morning. Moreover, "doctors are just more comfortable prescribing medication, because that's what they do for everything," Dr. [Alfred] Lewy [professor of psychiatry at Oregon Health and Science University] said.

Id. Accordingly, depression therapy currently remains focused, in large part, on medication with some use of light-box therapy.

SUMMARY

A light-monitoring system and method are described herein. Various embodiments of the apparatus and method may include some or all of the elements, features and steps described below.

As described herein, a light-monitoring system includes an apparatus with a power source (e.g., a battery); a light detector (e.g., a phototransistor); a computer processor coupled with the power source and in communication with the light detector and configured to receive and record light exposure detected by the light detector; an output device (e.g., a plurality of LED lights, a display screen, or a communication module for offloading data to a remote location) coupled with the computer processor; and a non-transitory computer-readable medium coupled with the computer processor and storing instruction code for summing the recorded light exposure from the computer processor over time and communicating a signal to the output device to generate and communicate a signal indicating that a cumulative threshold light exposure for achieving a health benefit (e.g., treatment of depression) has been reached.

A method for monitoring visible-light exposure includes positioning an integrative light monitor including a visible-light detector and an output device for indicating exposure to visible light; receiving and recording visible-light exposure received from at least one light source with the visible-light detector of the integrative light monitor; integrating the recorded visible-light exposure from each light source to produce a cumulative visible-light exposure value; comparing the cumulative visible-light exposure value with an established visible-light exposure target for a user to achieve a health benefit; and providing active and direct feedback from the output device to the user indicative of the cumulative visible-light exposure value in comparison with the established visible-light exposure target to empower the user to change behavior to achieve the benefit that is a consequence of reaching the cumulative visible-light exposure target.

In another method for monitoring light exposure, a user wears an integrative light monitor including a light detector. While the user wears the integrative light monitor, the user exposes him/herself to light from a first light source (e.g., an artificial light source, such as a light box), some of which is received and recorded by the integrative light monitor. The user also gains exposure to ambient light from a second light source (e.g., the sun while wearing the integrative light monitor outdoors), in which case, the recorded light exposure from the first light source and from the second light source is integrated to produce a cumulative luminous exposure value. The cumulative luminous exposure value can then be compared (directly or indirectly) with an established luminous-exposure target for achieving a health benefit; and an indication of the cumulative luminous-exposure value in comparison with the luminous exposure target can then be indicated (e.g., to the user). The integrative light monitor can also apply a minimum light-intensity threshold below which exposure is not likely to provide any benefit. Such low-intensity light can be excluded from the integrated record of exposure. The integrative light monitor may also afford some mechanism (e.g., indicator LED) to indicate to the user that the current light intensity exceeds the minimum threshold (e.g., 2,500 lux) to indicate thereby that the user is benefitting from the exposure.

The apparatus and method allow for cross-mode integrated monitoring of light from various sources (e.g., light box and natural sunlight) and exposure tracking to display incremental progress toward and achievement of a targeted dose of bright light exposure, e.g., effective for the treatment of seasonal affective disorder depression (SADD). Additionally, the apparatus for performing these functions can be comparatively simple and inexpensive, readily enabling low-cost purchase by patients and independent use after diagnosis and prescription of this treatment methodology by a physician (e.g., a psychiatrist) to treat depression or other disorder.

BRIEF DESCRIPTION OF THE DRAWINGS

FIG. 7 is a perspective view of a light-monitoring apparatus with four LED indicators.

FIG. 8 is a side view of the light-monitoring apparatus of FIG. 7.

FIG. 9 is a front view of the light-monitoring apparatus of FIG. 7.

FIG. 10 is a front view a light-monitoring apparatus with a radial LED ring that gradually illuminates around the perimeter of the window with increasing exposure to bright light.

FIG. 11 is a perspective view of a light-monitoring apparatus with a photovoltaic material acting as a light detector, or as a source of power, on its face.

FIG. 12 is side view of the light-monitoring apparatus of FIG. 11.

FIG. 13 is a front view of the light-monitoring apparatus of FIG. 11.

FIG. 14 is a top view of another embodiment of a light-monitoring apparatus that includes a photovoltaic panel.

FIG. 15 is a front view of the light-monitoring apparatus of FIG. 14.

FIG. 16 is a side view of the light-monitoring apparatus of FIG. 14.

Figure 1:
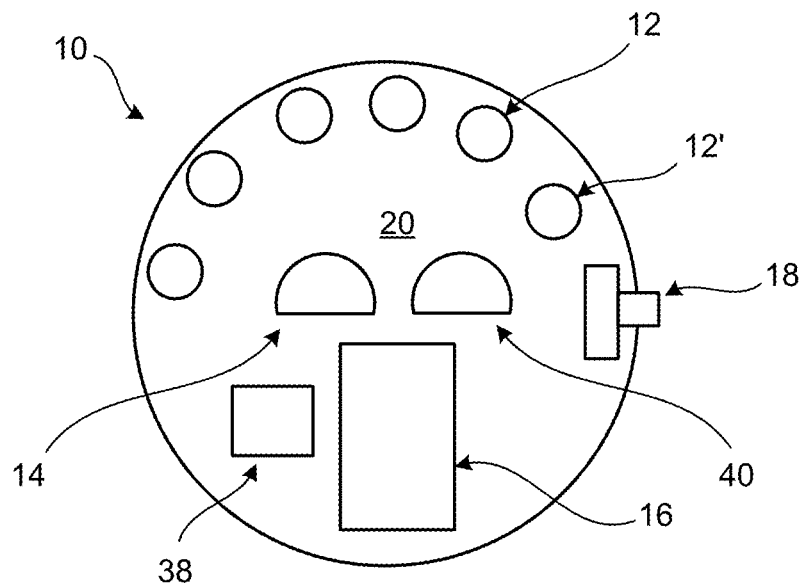
FIG. 1 is a front view of the internal components of an embodiment of a light-monitoring apparatus including a phototransistor 14, microcontroller 16, and an output device 12 in the form of a series of LED lights.

In the accompanying drawings, like reference characters refer to the same or similar parts throughout the different views; and apostrophes are used to differentiate multiple instances of the same or similar items sharing the same reference numeral. The drawings are not necessarily to scale, emphasis instead being placed upon illustrating particular principles, discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular shape is referenced, the shape is intended to include imperfect variations from ideal shapes, e.g., due to manufacturing tolerances.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to" or "coupled to" another element, it may be directly on, connected or coupled to the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Figure 2:
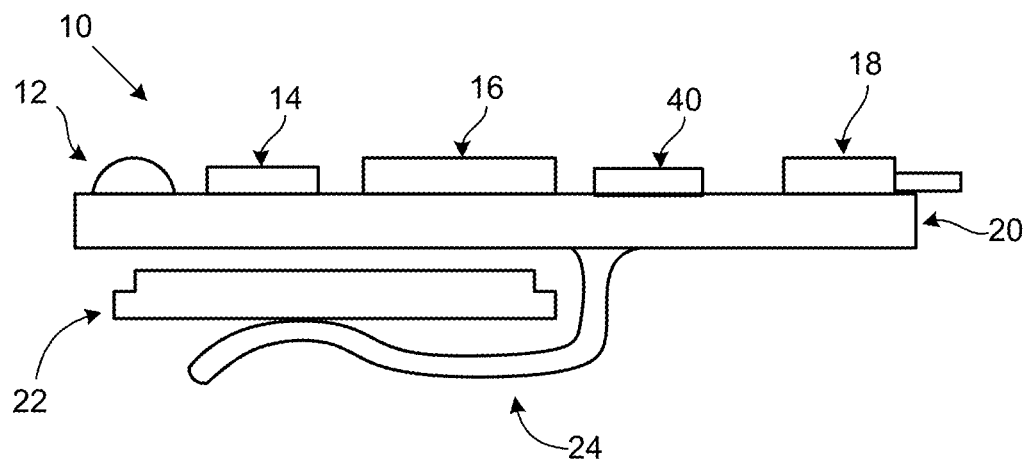
FIG. 2 is a side sectional view of the internal components of the light-monitoring apparatus of FIG. 1, also showing the battery 22 and the printed circuit board 20 on which the devices are mounted.

One embodiment of the integrative light monitor 10 (shown in FIGS. 1-5) is a wearable micro light sensor that can be about the size and shape of a tie tack or a U.S. quarter, though the monitor 10 can take any of a wide variety of shapes (e.g., round, square, rectangular, oval, contorted, emblematic, etc., some of which are shown in FIGS. 7-15) and sizes. It can be worn attached to a wearer's clothing, much like a tie tack or pin, facing forward in the same orientation as the eyes. The integrative light monitor 10 can be powered by a solar cell and/or a battery 22 (e.g., a CR1216 coin, CR2020, CR2025, CR2032, or button cell battery or a rechargeable cell battery), as shown in FIG. 2, and can measure the intensity and duration of bright light exposure received by the wearer's eyes by being oriented approximately in the direction of the wearer's gaze. The integrative light monitor 10, as shown in the Figures, can include, for example, some or all of the following components: at least one light detector 14 (e.g., a phototransistor); a power switch 18; a battery 22 (e.g., a 12, 20, 22, or 24 mm coin cell battery using a lithium compound for energy storage), which can optionally be accessible via access door 32; a processor (such as a computer microprocessor or an application-specific integrated circuit) and computer-readable memory (e.g., addressable semiconductor memory), both of which can be incorporated in a microcontroller 16; an output device 12 (e.g., a visual display, such as series of light emitting diodes); a radio-frequency wireless transmitter or an output port, such as a mini- or micro-USB port; an input device, such as a capacitive touch plate 34 (shown), a button, or an accelerometer 38 that can be used to evoke an indication of progress or can register input in the form, e.g. of a flick or tap by the user; a power input device for either wired or wireless recharging of a battery (e.g., a photodiode or photovoltaic cell for wireless optical recharging, a solenoid or transformer for wireless electrical recharging, or a receptacle enabling direct electrical connection for recharging, which can be the same as the electrical port used for data transmission); and an attachment mechanism 36 (e.g., a permanent magnet and ferromagnetic material, a pin, a chain, a band, or a clip). The electronic components can all be mounted and electrically interconnected on an integrated printed circuit board 20 contained inside the integrative light monitor's transparent front housing 26 and back 28 of the case and encircled by a bezel 30 that joins the front 26 and back 28 and rotates to activate the power switch 18.

Natural light exposure (e.g., from the sun) can be used as a replacement for or in combination with light box therapy. Examples of light boxes designed for light box therapy, are available from, for example, Light Therapy Products of Stillwater, Minn. Alternatively, other light sources can be used in combination with natural light.

In particular embodiments, as shown in the Figures, the integrative light monitor 10 can have a circular disk-shaped profile and a size approximately matching that of a U.S. quarter, though perhaps thicker (e.g., with a diameter of about 2.4 cm and a thickness of about 5 mm). The integrative light monitor 10 can include a pin, clip, magnet 36, or another clasp mechanism for affixing the integrative light monitor to clothing (e.g., a shirt, belt, shoes, backpack, hat, etc.); alternatively (or in addition), the integrative light monitor can have a loop through which a string, chain, tether, etc., can be strewn so that the integrative light monitor can be worn about a wearer's neck. In other embodiments the device 10 can be worn on the body of a user (e.g., wrapped around a user's wrist, incorporated into an earring and secured to a stem inserted through a user's earlobe, affixed to a ring worn on a user's finger, or affixed to a chain worn around the user's neck). In still other embodiments, the user may wear the device on the user's body underneath clothing; and the device can be calibrated to account for the amount of light blocked by the closing. Moreover, the device 10 can be configured to accept a plurality of interchangeable attachment mechanism, where the attachment mechanisms can be interchangeably pressure fit or locked into the body of the device 10 to allow the user to wear the device in different ways depending on factors such as attire, environment, and activity on a particular day.

Figure 3:
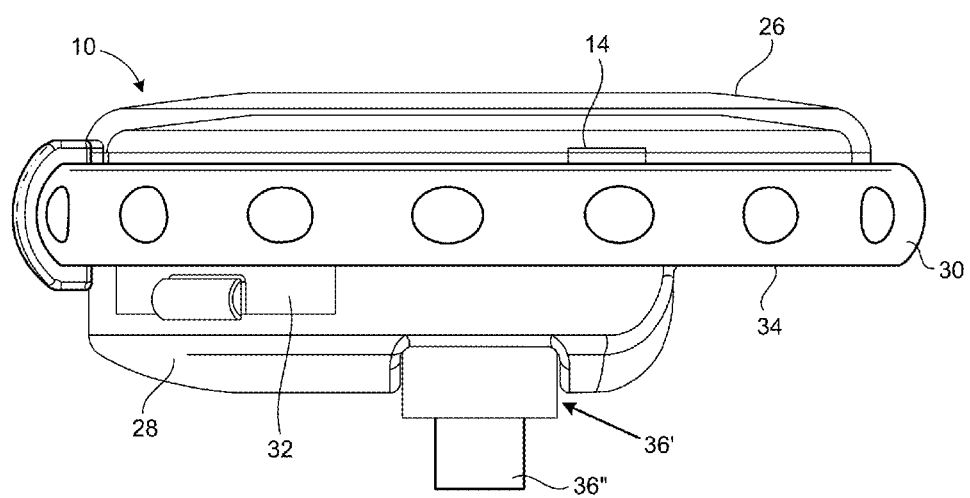
FIG. 3 is a side view of the light-monitoring apparatus of FIGS. 2 and 3 including the outer housing halves 26 and 28 joined by bezel 30, and showing a battery access door 32 and an affixed pin 36 for attachment to clothing.
Figure 4:
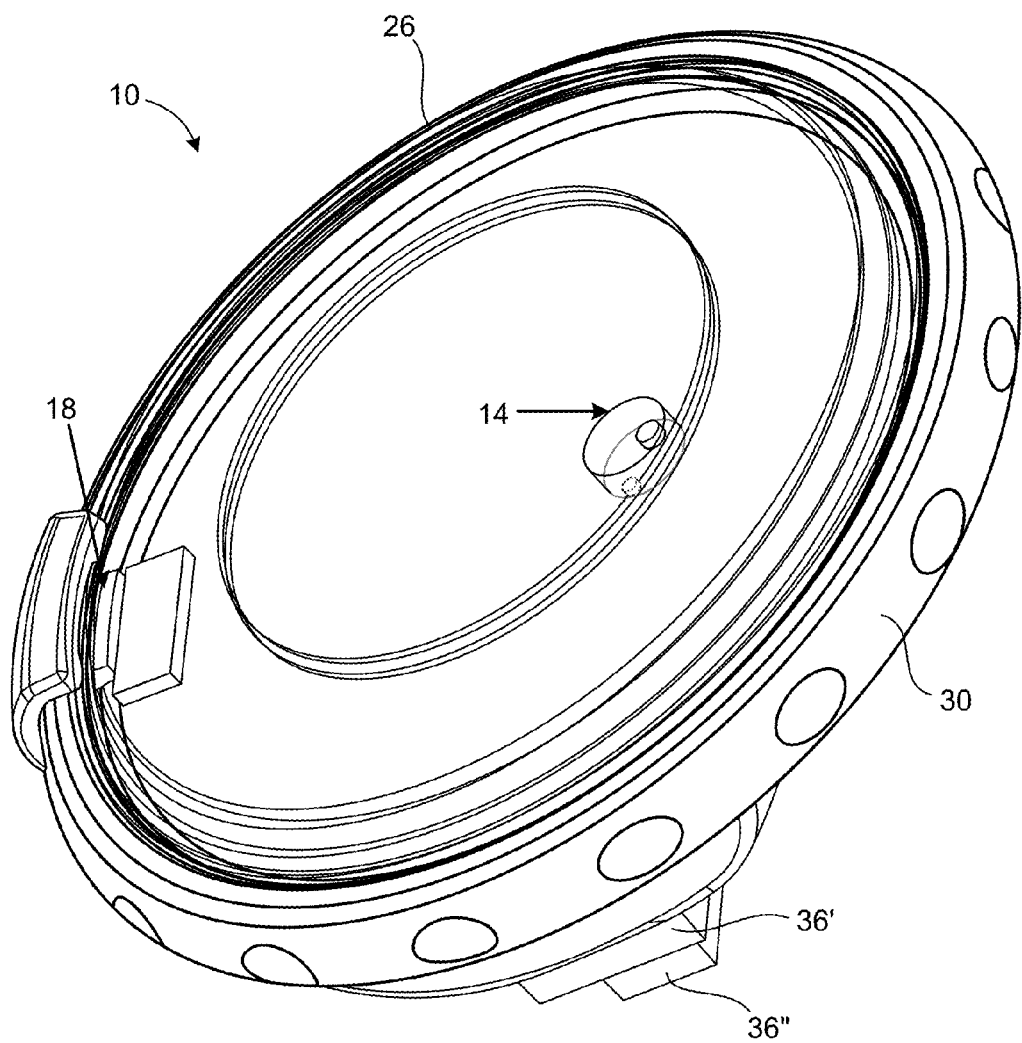
FIG. 4 is a perspective view of the top of the light-monitoring apparatus of FIGS. 1-3.
Figure 5:
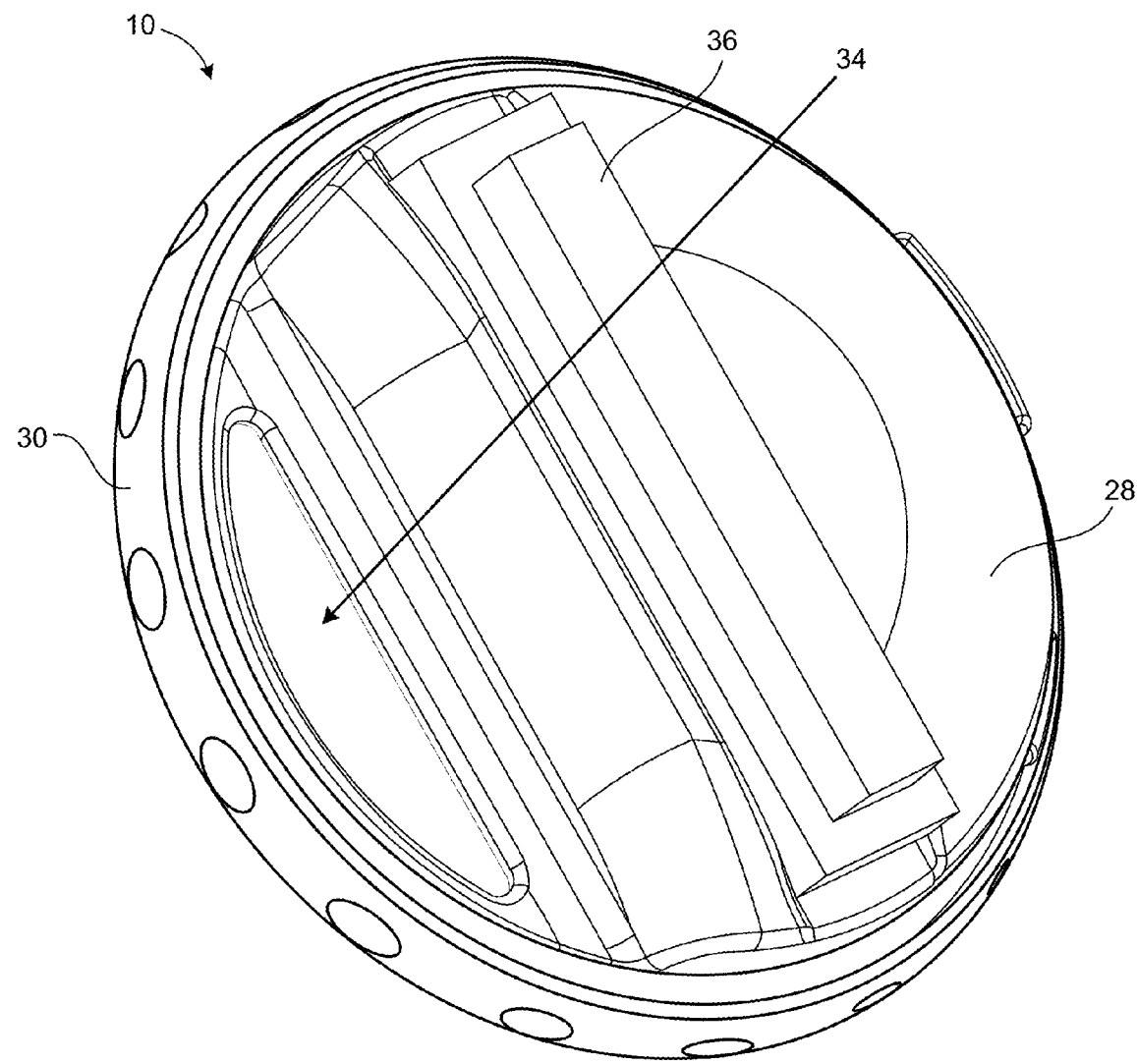
FIG. 5 is a perspective view of the back of the light-monitoring apparatus of FIGS. 1-4.

In one embodiment, as shown in FIGS. 3 and 4, a first magnetic material 36' (e.g., a permanent magnet or a ferromagnetic material that responds to a magnetic field) is embedded into the integrative light monitor, and a second magnetic material 36" (e.g., a permanent magnet if the first magnetic material is a ferromagnetic material or vice versa) to which the first magnetic material 36' can be magnetically secured can be positioned on an opposite side of clothing fabric (e.g., against the inside of a shirt pocket or opening or the underside of a collar) to allow the first magnetic material on the integrative light monitor to be magnetically secured thereto through the fabric. The first magnetic material 36' can be in the form of a flat plate of ferromagnetic material (e.g., iron, nickel, cobalt or rare-earth alloy) that is either attached to the back 28 of the integrative light monitor's packaging or embedded within the integrative light monitor's packaging. In some embodiments, the case of the battery 22, itself, can serve as the first magnetic material.

If the integrative light monitor is mounted via a magnetic attachment, a magnetic reed relay mounted on the printed circuit board 20 can be used to turn the integrative light monitor "on" only when the first and second magnetic materials are secured to each other. In other embodiments, as shown in the Figures, a bezel 30 can be provided at the perimeter of the device 10 and can be pivoted (rotated) along the perimeter in either direction to activate the power switch 18 to turn the power on and off.

In another embodiment, the device 10 can be mounted on the temple arm of a wearer's eyeglasses (e.g., non-shading prescription eyewear) with the light detector configured to face in the same direction as the wearer's eyes when wearing the eyeglasses to obtain a more accurate reading as to the light exposure at the eyes. In this embodiment, the light emitting diodes (LED's) or other display indicators can be provided in a straight-line orientation parallel to the temple arm.

Side views of an embodiment of the integrative light monitor 10 (with and without the housing) are provided in FIGS. 2 and 3, where the printed circuit board 20, the microcontroller unit (MCU) 16, the power switch 18, the LED's 12, the phototransistor 14, the battery 22, the battery holder 28, the battery access door 32, the capacitive touch plate 34, the ferromagnetic plates 36, the transparent front 26, the back 28 of the housing, and the bezel 30 are shown. The battery 22 can be advantageously mounted on an opposite side (e.g., a back side) of the printed circuit board from the other components or mounted in the clip or attachment mechanism, though the other components can be mounted essentially anywhere on the printed circuit board 20.

If the device 10 is to log light exposure over several days, then more than a single user input mechanism can be incorporated into the device 10 (e.g., more than a single capacitive touch plate 34) or the device 10 can be configured to recognize differentiating inputs (e.g., one tap versus two taps on the input mechanism for different inputs). The device 10 can include, e.g., multiple touch pads, push buttons or an accelerometer via which distinct motions can be differentiated), offering more than just the interrogate function, described above. Other commands that can be communicated via the user inputs include telling the device 10 to "start a session," "terminate a session," "re-initialize," (fresh start, clearing existing log) and optionally also "transmit" (e.g., if implemented in a scheme to transfer data to computer or cell phone).

The light detector can be in the form of a phototransistor 14, which is shown in FIGS. 1-4, or a series of phototransistors that can respectively record radiation across different ranges of the electromagnetic spectrum. In one embodiment, the phototransistor 14 has dimensions of about 2 mm×1.25 mm measured parallel to the plane of the printed circuit board 20) and is surface mounted on the printed circuit board 20. The front 26 of the integrative light monitor's housing is transparent near its upper edge where the surface-mount phototransistor 14 is positioned so as to expose the surface-mount phototransistor 14 to incoming light. The transparent front 26 of the housing also makes the light emitting diodes (LED's) 12, discussed below, visible through the housing by the user. In additional embodiments, the detector 14 can be mounted to the printed circuit board 20 via extended leads. The leaded detector 14 can be mounted anywhere on the circuit board 20, and its long leads allow it to poke up through the front 26 of the housing. By poking through the housing, the leaded detector 14 is readily exposed to incoming light.

In other embodiments, a rechargeable cell battery can be used in place of the button-cell battery as the power supply 22. The rechargeable cell includes an electrical connector (e.g., a micro-USB port) for coupling the cell to a voltage source for recharging the battery. Use of a rechargeable battery in the device design can ease design constraints aimed to limit demands on the battery. The rechargeable battery can be recharged each night or during the day (or at least once a week) to keep the device functioning. An advantage of using a rechargeable battery over a (non-rechargeable) conventional button-cell battery is that the device 10 would not need to be configured to be openable by a user to enable battery replacement.

In a particular embodiment, as shown in FIGS. 11-13, the light detector 14 comprises a photovoltaic material 56 (such as silicon or an LED) or several photovoltaic materials connected in series; and the luminous flux that is measured is a function of the known area of the photovoltaic material 56 and either the current generated, voltage generated, some combination of current and voltage, or other property related to the absorption of photons by the photovoltaic material 56. In this embodiment, a portion of the electric current generated by the photovoltaic material 56 as a consequence of light exposure can be used as a supplemental power source or can be directed to the battery 22 to recharge the battery 22 for continued operation of the device 10. The photovoltaic material 56 in this embodiment has a square face with a width, w, and a height, h, of 20-30 mm, while the device 10 (excluding the clip 54) of 3-9 mm. As shown in FIGS. 11 and 12, the LEDs 12 can be positioned about the perimeter of the device 10, or they may be interspersed among individual photovoltaic materials on the face of the device.

Another embodiment with a photovoltaic material 56, or several photovoltaic materials connected in series, acting as a detector 14 and, potentially, as a power source, is shown in FIGS. 14-16. In this embodiment, the photovoltaic material 56 is mounted in the casing 52 at the front face of the device 10; and the LEDS 12 can be mounted in the casing 52 about the perimeter of the device 10, or interspersed among individual photovoltaic materials on the face of the device. The dimensions of the device 10 in this embodiment can be substantially the same as in the embodiment described in the previous paragraph.

Where the device 10 is provided with an on/off switch (e.g., in the form of a depressible or slidable power switch 18 on the edge of the device), the device 10 can also include a dim "On" LED indicator 12' among the LED's 12 that illuminates to inform the wearer that the battery 22 is being utilized and to help ensure that the wearer does not forget to turn it off after use (e.g., after bright light exposure is complete for the day or after the target exposure is reached). Use of the "On" LED indicator 12' is particularly advantageous when used in conjunction with the use of a rechargeable battery, since battery drainage may be less of a concern when the battery 22 can be easily recharged. Alternatively, the device 10 can be configured so that the LED's illuminate or blink in response to user input to indicate that the device 10 is on and responsive.

Moreover, whether using a rechargeable battery or an ordinary coin or button-cell battery 22, where the device 10 may be shut down during use, the device 10 can include nonvolatile memory; and the microcontroller unit 16 can be programmed to save the accumulated light-exposure value to the nonvolatile memory during power down (e.g., activated with the detection of a gradual decline in the supply voltage over, e.g., a period on the order of milliseconds). To facilitate this capacity for automatic saving of data, the device 10 can be designed so that power loss is drawn out over time during a shutdown. In one embodiment, when the device 10 is restarted and power restored (e.g., by coupling with the reciprocal magnet or by activating the on/off switch 18), the microcontroller unit 16 can recall the accumulated light-exposure value and resume logging of light exposure (in its memory) toward the designated target exposure level. In this embodiment, where saving the light-exposure value is the default mode of operation, means for "resetting" the accumulated light exposure (e.g., at the start of a new day) can be provided, e.g., in the form of another button or via a coded activation of the button (e.g., depressing the button for multiple seconds, depressing the button multiple times or depressing multiple buttons simultaneously). If saving of the accumulated light exposure is not automated with powering down the device 10, a "save" button can be provided on the device 10 or a code for saving can be provided on one or more buttons shared with other functions. In these embodiments, the device 10 need not include a dedicated on/off switch (or other mechanism), as the device is powered and rendered operational by sun exposure on a photovoltaic material or when power is available from an integrated battery.

The light-monitoring device 10 and associated electronics (e.g., a computer processor, memory and software non-transitorily stored on a computer-readable medium, as discussed below) measure both the instantaneous light intensity and the integral of light intensity over a period of time. Exemplary computer electronics and communication technologies that can be incorporated in or used with this integrative light monitor device 10 are described in the sections entitled, "Computers, software, storage media and other components" and "Network connections and communications", below. The processor, which can be integrated into a microcontroller 16, can be coupled with the detector(s) {e.g., phototransistor(s)] 14 and, in particular embodiments, with an accelerometer 38, and can record and integrate illuminance readings from the detector 14 to produce a cumulative luminous exposure value per instructions stored as software code on the computer-readable medium, which also is coupled with the processor (and which can also be incorporated into the microcontroller 16). Where an accelerometer is used, its readings can be recorded and paired with the illuminance readings.

Pursuant to the software code processed by the processor, the processor compares the cumulative luminous exposure value with a chosen target value and communicates whether that target value has been reached or whether a particular increment toward that target value has been reached. That communication from the processor can be received, e.g., by a computer, cell-phone or custom display (e.g., LCD, E-Ink, etc.), by a bank of lights (e.g., LED's 12, as shown in the Figures), an audio output (e.g., a speaker or bell), or a vibration mechanism (e.g., a piezoelectric plate) serving as a human interface to communicate the results to a wearer.

The integrative light monitor device 10 can perform as a threshold device that will alert the wearer (e.g., through light activation, color change, or audible signal) when one of the several states associated with medical/psychiatric benefits has been reached. The integrative light monitor device 10 can register, for example, an exposure of 12-24 million lux-seconds. In particular embodiments, the targeted exposure is 18 million lux-seconds (e.g., exposure to 10,000 lux for 30 minutes or 2,500 lux for 120 minutes). Alternatively or in addition, the integrative light monitor device 10 can register, for example, an instantaneous exposure of 2,500 lux, to signify that the light intensity to which the user is being exposed is sufficient to achieve medical/psychiatric benefits if maintained for sufficient duration. The device 10 can also generate a signal for UV exposure, indicating, for example, (a) that the sun is sufficiently strong to produce vitamin D, (b) when the recommended vitamin D production has completed, or (c) when the user is likely to suffer a sunburn or other skin damage that may, for example, lead to melanoma or skin cancer.

These bright-light exposures can be used as therapy for various mood disorders, including major depressive disorder, which includes the presence of two or major depressive episodes (with an interval of at least two months between episodes), wherein the major depressive episodes can be diagnosed, e.g., with a finding of the presence five or more of the following symptoms during the same two-week period [representing a change from previous functioning and wherein at least one of the symptoms is either (a) depressed mood or (b) loss of interest or pleasure]:

1. depressed mood most of the day, nearly every day, as indicated by subjective report (e.g., feels sad or empty) or by an observation made by others (e.g., appears tearful);
2. markedly diminished interest or pleasure in all, or almost all, activities most of the day, nearly every day (as indicated by subjective account or by observation by others);
3. significant weight loss when not dieting or weight gain (e.g., a change of more than 5% of body weight in a month), or decrease or increase in appetite nearly every day (or, in the case of children, a failure to make expected weight gains);
4. insomnia or hypersomnia nearly every day;
5. psychomotor agitation or retardation nearly every day (observable by others, not merely subjective feelings of restlessness or being slowed down);
6. fatigue or loss of energy nearly every day;
7. feelings of worthlessness or excessive or inappropriate guilt nearly every day, which is not merely self-reproach or guilt about being sick;
8. diminished ability to think or concentrate, or indecisiveness, nearly every day (either by subjective account or as observed by others); and
9. recurrent thoughts of death (not just fear of dying), recurrent suicidal ideation without a specific plan, or a suicide attempt or a specific plan for committing suicide.

Bright-light exposure can also be used to treat seasonal and non-seasonal depression. Bright-light exposure is also effective in the alleviation of subclinical seasonal mood changes ("winter blues") that are extremely common in populations that experience a significant decrease in sunlight during winter months. Additionally, exposure to bright light during the day [and prevention of bright-light exposure near (e.g., within an hour or several hours of) the time of sleep onset] can provide a beneficial effect in treating insomnia associated with circadian rhythm difficulties. Consequently, use of the integrative light monitor device 10 in conjunction with light exposure by individuals with these conditions can also be advantageous. By signaling when a therapeutic "dose" is reached, the integrative light monitor also allows the wearer to limit excessive exposure to sunlight through the use of sunglasses and sunscreen at an appropriate time. In other embodiments, the device can be used to treat, such as insomnia, attention-deficit hyperactivity disorder (ADHD), dementia in the elderly, bulimia nervosa, severe premenstrual syndrome, and bipolar disorder.

In a particular embodiment, the integrative light monitor device 10 can include a series of lights (e.g., four to six lights) in the form of miniature light-emitting diodes (LEDs) 12 arranged, e.g., in a half circle arch on a face of the integrative light monitor device 10. Where four LEDs 12 are used, they can be arranged in a square pattern with one at each corner of the square like the configuration of holes found in a typical clothing button, as shown in FIGS. 7-9. In the device 10 of FIGS. 7-9, the LEDs 12 are covered by a transparent or frosted lens 26 mounted in a brushed aluminum casing 52 on the front face of the device 10. The device 12 also includes a clip 54 so that it can be clipped, e.g., to a user's clothing; and this embodiment of the device 12 can have a diameter, d, of 20-30 mm.

Where five lights 12 are provided for indicating cumulative exposure and where the targeted luminous exposure is 18 million lux-seconds, an additional LED can light up with each incremental exposure of 3.6 million lux-seconds such that the full array of lights will be lit when the 18 million lux-second target is reached and the progress there toward can be incrementally monitored. The integrative light monitor device 10 can also include a power on/off switch 18, which when activated (e.g., shifted or depressed), can initiate an electronic interrogation, wherein power from the battery 22 is confirmed (activating the power-indicating amber LED 12'), voltage from the battery 22 is measured for adequacy (triggering blinking of the LED's 12 if voltage is inadequate), and cumulative light exposure since startup is ascertained from the memory (turning on some or all of the LED's 12 to indicate the amount of light exposure). In an alternative embodiment, the switch 18 is a capacitive-touch switch built into the printed circuit board 20.

In the embodiment of FIG. 10, the LED indicator 12 is in the form of a ring where sections of the ring sequentially illuminate with cumulative light exposure until the entire ring is illuminated, indicating that the target exposure is reached.

In one embodiment, the LED display 12 can be operated by depressing a push-button, which turns on an amber LED 12'; on the integrative light monitor, wherein the amber LED 12' remains lit to indicate that the integrative light monitor device 10 is powered and operating properly. A plurality of green LED's 12 on the integrative light monitor sequentially turn on to indicate progress toward a light-exposure goal. In an embodiment with five progress LED's 12, one lit progress LED 12 indicates ¼ completion; two lit progress LED's 12 indicate ½ completion; . . . and five lit progress LED's 12 indicate that 125% of the exposure goal has been achieved. The fourth LED 12 (indicating 100% of the target dosage) can provide a distinctive light color (e.g., red) to provide a distinctive "completion" signal.

An additional indicator (e.g., LED) or a distinctive indication from the existing indicator(s) can be provided to indicate the intensity of the incident light (e.g., indicating whether it meets or exceeds 2500 lux), as determined by the microcontroller, to thereby indicate whether, e.g., the intensity of the incident light is above a minimum threshold to produce a substantial benefit for the user; and the microcontroller can be programmed to ignore incident light intensities below the minimum threshold and to only record intensities at or above the threshold.

The LED's 12 can be wired to remain activated to show progress for no more than several (e.g., three) seconds in response to the user activating the power switch/button 18 to preserve battery power. Alternatively, the LED's 12 can be configured to remain lit only as long as the power switch/button 18 is depressed. To warn a user of low-battery power, all LED's 12 can be programmed to blink or change color in response to the usual "display_on" power switch/button activation.

In other embodiments, light exposure can be weighted as a function of time. Multiple studies have demonstrated that bright-light therapy for depression is most effective when administered in the morning and that early morning light is more effective than late morning light (bipolar disorder may be an exception, with perhaps a better response to mid-day light). Efficacy of the therapy is further increased if the timing of light therapy is adjusted based on an individual's circadian rhythm, either through measurements of melatonin peaks or through self-administered circadian-rhythm questionnaires. A log of the timing of light exposure allows the user, alone or in consultation with a clinician skilled in the use of light therapy, to maximize benefits of light exposure.

Figure 6:
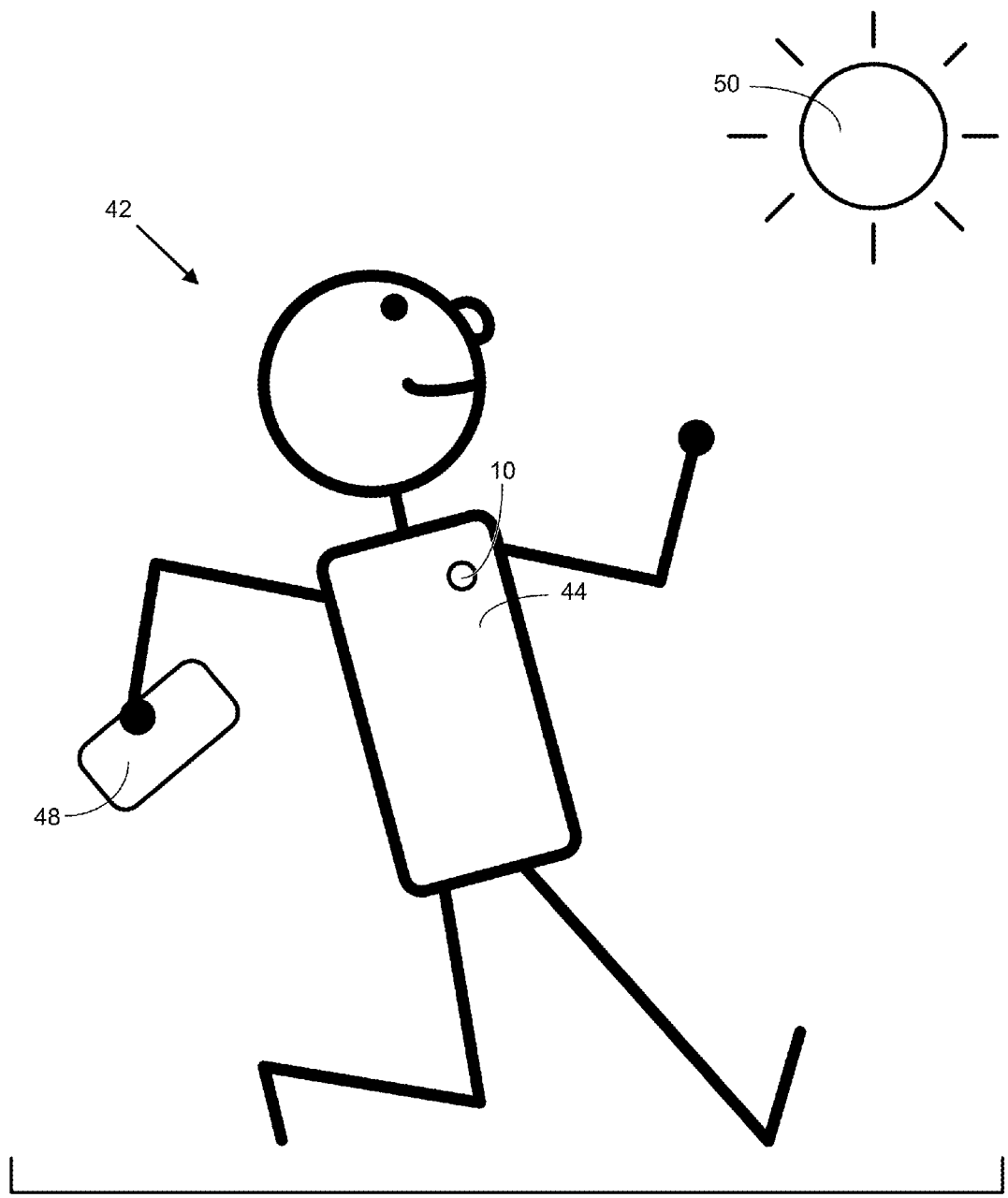
FIG. 6 is an illustration of a wearer of the light-monitoring apparatus receiving light exposure from the sun, where the light-monitoring apparatus is communicating with the wearer's smart phone.

Accordingly, in a method for monitoring light exposure through the eyes, the monitor records a time integral of exposure with accumulations time-stamped so as to make a record of the time-of-day when exposures occurred. These measurements may occur at regular intervals, e.g., every second, every minute, or timings in between, or at other irregular intervals that may be proportional to light exposure (i.e., more frequent readings taken in bright light or coinciding with other environmental factors). Accordingly, periodic readings of light exposure can be recorded in a database along with a current time stamp. This recorded data can be communicated to other electronic devices (e.g., to a smart phone; to "cloud storage" via the internet, via cellular data network, or via similar means and methods; or to a laptop, desktop or tablet computer) for remote display, processing and/or storage. An illustration of a user/wearer 42 of the device 10 (here, on his clothing 44) equipped with a smart phone 48 that is in (e.g., Bluetooth) communication with the device 10 as the wearer 42 is exposed to light from the sun 50 is provided in FIG. 6.

In additional embodiments for monitoring light exposure through a user's eyes, the light-monitoring device 10 or another electronic device 48 in communication with the light-monitoring device receives input from the user 42 to indicate the timing and quantity of any supplemental treatments received by the user (e.g., supplemental products, such as melatonin, ingested by the user). In one embodiment, the user 42 inputs this information via a smart phone 48 using an "app" that includes instructions for requesting and receiving this information via an on-screen user interface. The smart phone 48 can be in wireless communication with the light-monitoring device 10, and the app or another software component, when executed by a processor, uses the input to better tailor the optimal light exposure for the individual user 42. If, for example, light therapy is working somewhat for a user 42, though not ideally, a mental healthcare provider can adjust the user's treatment program, e.g., by adding melatonin supplements or other supplements/drugs, such as anti-depressant drugs, to the treatment program. The user 42 can be instructed to ingest the melatonin supplements at a time that coincides optimally with the user's circadian rhythm. In other embodiments, the supplements can be taken to alter the user's circadian rhythm or to shift the optimal timing of exposure to bright light. In additional embodiments, use of the supplements can reduce the user's target bright-light exposure level.

In additional methods for monitoring light exposure through a user's eyes, physical activity is monitored concurrently using an accelerometer 38 or similar component(s) incorporated within the device 10, wherein the data from the accelerometer 38 or from another component is fed to the computer processor. In this embodiment, the correlation between light exposure and physical activity can be used to better monitor and treat depression or other physical or mental illnesses. For example, detection of a high level of activity can be correlated with successful treatment, while detection of a low level of activity may trigger the medical provider to increase the targeted light exposure or to prescribe supplemental treatments in an effort to improve the user's condition. Moreover, in particular embodiments, the accelerometer 38 can also be used as an input device, as the user can flick or tap the device to indicate input.

In still more methods for monitoring light exposure through the user's eyes or on the user's skin, ultraviolet (UV) light is concurrently and separately measured by the device 10 (apart from concurrent measurements of total light exposure or of exposure to light in the, e.g., visible range) using a separate detector 40 (e.g., a UV photodiode) for the purpose of preventing harmful levels of UV exposure during light exposure that could lead to sunburn, skin cancer, etc. UV-light exposure approaching harmful levels can be communicated by making a mobile device beep; ring; vibrate; display a message; receive a text message, email, call, or other sort of notification; or via display in a mobile or computer application or on the device, itself.

Records of UV light exposure can also be used to determine and record what percentage of light exposure was obtained through natural sources, which may generate UV light, and artificial sources, which may not generate UV light. These correlations may, therefore, allow one to recognize that light exposure is from a natural source if UV light is concurrently detected or that light exposure is from an artificial source if no (or only smaller amounts of) UV light is detected when exposure to light at other wavelengths is detected. The user's program may be adjusted, for example, to target a higher ratio of natural light exposure, which may provide greater benefits than artificial light.

In one embodiment, a first detector 14 measures light exposure in the visible range (about 400 nm to about 700 nm) but not in the UV range (about 10 nm to about 400 nm), so it detects light from light boxes (which produce in the visible spectrum) as well as the visible-light portion of the radiation emitted from the sun, while the second detector 40 measures light in the UV spectrum but not in the visible spectrum. In this embodiment, the balance of light from artificial and natural sources is proportional to the cumulative exposures tallied from the first detector 14 and second detector 40, respectively.

In an alternative embodiment, either the first detector 14 or the second detector 40 detects light across both the visible and UV ranges, while the other detector detects light in only one of these ranges. Where, for example, the first detector 14 detects radiation across the visible and UV spectrums while the second detector 40 detects only radiation in the UV range, the cumulative exposure derived from readings from the second detector reflects cumulative exposure to sunlight. Meanwhile, cumulative exposure to light from artificial sources (e.g. light boxes) can be derived from the difference or ratio in cumulative exposure totals detected by the first and second detectors 14 and 40. In other embodiments, the detector can have a design similar to the image detector of a VGA camera, where pixel resolution of red, green, and blue is possible with a single detector; or a series of filters that filter different wavelength ranges can be placed over parts or all of a detector.

Alternatively, or in addition, monitoring light exposure includes concurrent measurement of UV light by the second detector 40 to determine whether the UV light intensity is sufficient for vitamin D3 production. To determine whether the UV light intensity is sufficient, the device can measure the UV index, for example, where a value above 3 is known to be sufficient. Appropriate light exposures may be, e.g., 10-15 minutes per day for three days a week, though the timings may be different depending on the user. Reaching the targeted UV exposure can be communicated by making a connected mobile device 48 (e.g., connected via Bluetooth or other form of wireless communication) beep; ring; vibrate; display a message receive a text message, email, call, or other sort of notification; or by generating a display indication in a mobile or computer application (e.g. on a smart phone) or on the light-monitoring device 10, itself.

In other embodiments, the device 10 can include multiple light sensors, each equipped with a light filter to detect light in different wavelength bands (e.g., light of different colors). In this embodiment, a detector 14 configured to receive light from a filter that passes only blue light can, for example, be weighted higher (i.e., be multiplied by a greater weighting factor) than light detected by detectors 14 configured with respective light filters to receive light in other colors, as exposure to blue light may be more beneficial than exposure to light of other colors. Accordingly, the light exposure detected by each detector 14 can be multiplied by an appropriate weighting factor (determined by the efficacy of the respective wavelength band); and those multiples can be integrated until an overall daily target is reached.

In additional embodiments, data regarding daily integrated light exposure and data regarding the time of day of light exposure from the device 10 are used to calculate and display (e.g., on the display of another device 48, such as a computer, tablet or smart phone in communication therewith) a user's day-by-day rating of (1) actual light exposure as a percent/fraction of an optimal dose and (2) the closeness of fit between actual time of bright-light exposure and optimal timing of bright-light exposure. Standard optimal values for dosage (e.g., 10,000 lux for 30 minutes) or combinations of dosage and timing (e.g., 5,000 lux for 60 minutes within one hour of sleep offset) may be provided; or the values may be individualized based on treatment history and measures of circadian rhythm. An overall numerical score representing "light effectiveness" may be calculated, the components of which may include the percent/fraction of an optimal dose weighted by the time of day that the light was received and factored into measuring the user's progress toward an exposure target. For most people, light received within one hour after waking from sleep may be weighted with a factor of 1.0. Light received within another hour (an additional hour after sleep offset) may be weighted, e.g., at or close to 1.0, 0.9, 0.8, or 0.7. Light further removed from sleep offset may be weighted less (e.g., at 0.5); and further out, such as in the evening, the light may be excluded by a weighting factor of 0.0.

This change in weighting factor may increase or decrease linearly, quadratically, exponentially, logarithmically, or via some other relationship as a function of time-of-day. For some users, light exposure later in the day may be more beneficial than light earlier in the day; and the relationship may be determined based upon dim-light melatonin onset (DLMO) of 10 pg/ml, 2 pg/ml, or other significant concentration, where the weighting factor can be 1.0 within an hour of DLMO, with decreasing effectiveness away from this time.

Another method of determining an optimal (or near-optimal) time of day for bright-light exposure is via user responses to circadian-rhythm questionnaires, such as the Morningness-Eveningness Questionnaire, which is a self-assessment described in Horne and Ostberg, "A self-assessment questionnaire to determine morningness-eveningness in human circadian rhythms," International Journal of Chronobiology, 4(2), 97-110 (1976). Again, the user can be queried and can provide responses via a separate electronic device, such as a mobile phone or networked computer, in communication with the light-monitoring device 10. Examples of light-effectiveness or closeness-of-fit display methods include (a) a graph with a bar indicating optimal timing of bright-light exposure and a bar indicating actual timing of bright-light exposure, (b) a digital or analogue display of the time interval between optimally timed completion of bright-light exposure and actual completion of bright-light exposure, (c) a calculation of percent overlap between optimal timing of bright-light exposure and actual timing of bright-light exposure, (d) a line graph of actual timing of bright-light exposure either superimposed or next to a line graph of optimal timing of bright-light exposure, or (e) other graphical representation of linear or non-linear mapping between optimal and actual timing of bright-light exposure.

Still another method of determining an optimal (or near-optimal) time-of-day for bright-light exposure is to utilize data recorded by the device to tailor the optimal timing and dosage of light exposure incorporated into the program for the specific user 42, which may include (a) mood polls in which the user 42 participates via an external device 48, such as a smart phone or computer, where the recorded mood is correlated with contemporaneous light exposure; (b) data upload from the device 10/48 to a medical provider or other caretaker for remote monitoring and investigation of bright-light exposure, which can be sent via mobile phone, computer, or other means; (c) data summaries of bright-light exposure, where the data summaries are published or shared with others via social media or similar sites to encourage the user 42 through behavioral reinforcement (e.g., positive feedback) or contact with friends, family, or other important people; and/or (d) presentation of rewards to the user 42 or other reinforcement mechanisms to encourage the user 42 to obtain the optimally targeted light exposure.

In still another method, data recorded by the device is communicated and utilized such that the user's medical provider or other person administering or monitoring treatment can remotely monitor the user's compliance with the treatment, including monitoring the amount of light received per day, the time that the light was received, the user's physical activity level, the user's exposure to particular types of light (e.g., ultraviolet), and/or the user's mood, feelings, or other physical or mental characteristics. Where exposure to ultraviolet light is detected, that exposure can be correlated with exposure to natural (sun) light, as artificial light from light boxes typically is entirely or nearly entirely within the visible light range. In additional embodiments, this data is shared with friends (e.g., via social media) or otherwise updated to a website or other online platform viewable by others to generate additional motivation for the user.

Moreover, the data stored in memory on the device can be communicated and utilized such that the medical provider or other person administering or monitoring treatment (e.g., via a smart phone 48) can remotely alter the user's treatment plan, communicate with the user 42, or provide other forms of information based on the data collected by the device 10 to (1) increase the user's target light dosage, if found to be insufficient; (2) decrease the user's target light dosage, if found to be excessive; (3) alter the user's targeted optimal time of day to receive light, which can be moved earlier or later, depending on the user's response; (4) coordinate or suggest other forms of medication or supplements for the user 42, such as anti-depressant medication, melatonin supplements, or others; (5) schedule or monitor the user's activity, which can include general daily activity or exercise; (6) schedule or suggest a follow-up exam, phone conversation, chat, email, or other mode of conversation between the user 42 and provider.

In other embodiments, an electronic display (e.g., such as those manufactured by E Ink of Cambridge, Mass.) can be used to display light exposure measurements and other indicators in place of the LED's, described above. Using an E Ink display, where colors or darkness levels in pixelated regions in a display area can be established by attracting pigment that is dark or light (or of a particular color) within microcapsules via application of an electric field, which enables very low-energy operation. While other embodiments may only activate the indicators/display when "interrogated" via an activation from the user (to save power), a zero-power display, such as those manufactured by E Ink, allow for continuous display.

The integrative light monitor device 10 can have a simple construction and can be relatively inexpensively produced; and, by eliminating the uncertainty of dosing, allow sunlight exposure to safely, easily, and enjoyably replace the tedium of sitting at a desk or table tethered closely to a light box. The integrative light monitor device 10 can, however, also respond to artificial light of sufficient intensity, allowing the wearer to move freely between artificial and natural light while continuing to monitor adequate light exposure. If, for example, a wearer sits in front of a light box at 10,000 lux for 15 minutes and also is subject to an additional 9 million lux-seconds of light exposure while, e.g., walking to work on a sunny day, the integrative light monitor device 10 can sum those exposures and accurately determine that the cumulative exposure satisfies an 18 million lux-seconds target. The integrative light monitor device 10 can be packaged with an instruction sheet that explains proper timing of light exposure for optimal benefits and the potential side effects of excessive light exposure. Alternatively, instructions can be conveyed via the software/app that is operated in communication with the device 10 and that is viewed by the user.

In various embodiments, the integrative light monitor device 10 can communicate the light-exposure data to other external electronic components (e.g., to a smart phone, to "cloud storage" via the internet, or to a laptop, desktop or tablet computer) for remote display, processing and/or storage. The data can be communicated via an integrated communication device (e.g., a wireless transmitter, which can include and utilize near-field technology or low-energy Bluetooth technology, or a USB port) in the integrative light monitor device 10.

In particular embodiments, the device 10 can connect, not only to a computing/communication device 48, such as a mobile phone or computer, but also to either a light box or other source of bright light within the home or elsewhere using Bluetooth transmitters/receivers, another wireless technology, or some proprietary protocol, wherein the light box or other light fixture responds to the device with specificity as to the person using the identified device. For example, the light box can be programmed automatically turn on if the device indicates that a user (associated with the device) has obtained insufficient light exposure (i.e., has not yet reached a targeted threshold for bright-light exposure); similarly, the light box can be programmed to beep or blink to remind the user to use light therapy. These methods can work the same way for a light fixture within a home; for example, a ceiling light in the kitchen or bathroom could switch to "bright mode" if it detects a device associated with a user in the area with insufficient light exposure. Such integrated fixtures can eliminate the separate need for a light box.

Computers, Software, Storage Media, and Other Components

The systems and methods of this disclosure can be implemented in a computing system environment. Examples of well known computing system environments and components thereof that may be suitable for use with the systems and methods include, but are not limited to microcontrollers, personal computers, server computers, hand-held or laptop devices, tablet devices, multiprocessor systems, microprocessor-based systems, set top boxes, programmable consumer electronics, network PCs, minicomputers, mainframe computers, distributed computing environments that include any of the above systems or devices, and the like. Typical computing system environments and their operations and components are described in many existing patents (e.g., U.S. Pat. No. 7,191,467, owned by Microsoft Corp.).

The methods may be carried out via non-transitory computer-executable instructions, such as program modules. Generally, program modules include routines, programs, objects, components, data structures, and so forth, that perform particular tasks or implement particular types of data. The methods may also be practiced in distributed computing environments where tasks are performed by remote processing devices that are linked through a communications network. In a distributed computing environment, program modules may be located in both local and remote computer storage media including memory storage devices.

The systems (e.g., of the "client" and "server") and methods of this disclosure may utilize a computer (e.g., in the form of a microcontroller) to carry out the processes described herein. Components of the computer may include, but are not limited to, a computer processor, a computer storage medium serving as memory, and coupling of components including the memory to the computer processor. A microcontroller is a small computer including a single integrated circuit containing a processor core, non-transitory computer storage media (memory), and programmable input/output peripherals and can be used as an embedded system. The microcontroller memory can include both permanent (non-volatile) read-only memory (ROM) storing pre-programmed software in the form of a compact machine code as well as volatile read-write memory for temporary data storage. The microcontroller can also include an analog-to-digital converter if the light detector to which it is electronically coupled transmits its illumination data in analog format as well as a programmable interval timer to control, e.g., the duration of activation of the indicator LED's.

The various processes described in the descriptions of this disclosure can be encoded as software instructions in memory and executed by a processor to carry out the processes.

Network Connections and Communications

The computing device (e.g., computer or smart phone) can operate in a networked environment using logical connections from a server to one or more remote client computers (e.g., microcontrollers embedded in discrete light-monitoring devices). The remote computer can be a personal computer, a server, a router, a network PC, a peer device or other common network node, and typically includes many or all of the elements described relative to the above-described computer. The networked environment can include a local area network (LAN), a wide area network (WAN), and/or other networks. Such networking environments are commonplace in offices, enterprise-wide computer networks, intranets and the internet.

When used in a LAN-networking environment, the computer can be connected to the LAN through a network interface or adapter. When used in a WAN-networking environment, the computer can include a modem or other communication interface for establishing communications over the WAN (e.g., over the internet). The communication interface, which can be internal or external to the computer housing, can be connected to the system bus via the user-input interface or another appropriate mechanism.

In an embodiment of a WAN environment, light-exposure data from the light-monitoring device can be uploaded via a transmitter and the internet to a computer server; and a user (via a client computing device connected with and in communication with the internet) accesses that data using, e.g., an internet browser (such as Internet Explorer from Microsoft, Firefox from Mozilla, or Chrome from Google) via hypertext transfer protocol (HTTP) communications or via communications generated and/or received by a software program, such as an email application (e.g., Microsoft Outlook) that can be stored in the computer's memory. The computer server can be a computer including memory storing a web server application, such as the Apache HTTP Server. The client computer can send an HTTP GET request to the server via the communication media that form the internet, and the participating server can respond to the client computer via the internet with an appropriate HTTP response.

HTTP is a request-response protocol standard for client-server computing. In HTTP, a personal computer running a web browser, for example, acts as a client, while a computer hosting a web site acts as a server. The client submits HTTP requests to the responding server by sending messages to it. The server, which stores content (or resources) such as HTML files and images, or generates such content on the fly, sends messages back to the client in response. These returned messages may contain the content requested by the client or may contain other kinds of response indications. Between the client and server, there may be several intermediaries, such as proxies, web caches or gateways. In such a case, the client communicates with the server indirectly, and only converses directly with the first intermediary in the chain.

An HTTP request message from the client can include the following: (a) a Request line that requests a resource (such as an image); (b) Headers; (c) an empty line; and, optionally, (d) a message body. The HTTP Headers form the core of the HTTP request, as they define various characteristics of the data that is requested or the data that has been provided. The HTTP Headers can include a referrer that identifies, from the point of view of an internet web page or resource, the address of the web page (e.g., the URL) of the resource that links to it. By checking the referrer, the new page can determine the source of the request message. A variety of different request protocols exists; for example, a "GET request" requests a representation of the specified resource from the host.

In describing embodiments of the invention, specific terminology is used for the sake of clarity. For the purpose of description, specific terms are intended to include at least technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A method for monitoring visible-light exposure, comprising:
    positioning a light monitor including a visible-light detector and at least one of (a) an output device and (b) a communication device;
    receiving and recording visible-light exposure received from at least one light source with the visible-light detector of the light monitor;
    integrating the recorded visible-light exposure from each light source to produce a cumulative visible-light exposure value;
    comparing the cumulative visible-light exposure value with an established cumulative visible-light exposure target for a user to achieve a health benefit; and
    providing active and direct feedback from at least one of:
    (a) the output device and
    (b) a mobile device transported by the user and in communication with the communication device
    to the user, wherein the feedback is indicative of the cumulative visible-light exposure value in comparison with the established visible-light exposure target to empower the user to change behavior to achieve the benefit that is a consequence of reaching the established cumulative visible-light exposure target.

2. The method of claim 1, wherein the light monitor is worn on or worn as part of the user's clothing, eyeglasses, or body.

3. The method of claim 2, wherein the established cumulative visible-light exposure target is in the range of 12-24 million lux-seconds.

4. The method of claim 1, wherein the cumulative visible-light exposure value is visually displayed by at least one of (a) the output device and (b) the mobile device.

5. The method of claim 1, further comprising:
applying a minimum light-intensity threshold to the visible-light exposure to exclude visible-light illuminance below the minimum light-intensity threshold; and
providing active and direct feedback from at least one of (a) the output device and (b) the mobile device to the user indicating whether instantaneous light exposure is at least as great as the minimum light-intensity threshold to empower the user to change behavior so as to achieve the established cumulative visible-light exposure target.

6. The method of claim 1, wherein the light monitor is used by a user suffering from a condition selected from a form of depression, sleep disorder, circadian rhythm disorder, attention-deficit hyperactivity disorder, dementia, bulimia nervosa, severe premenstrual syndrome, and bipolar disorder.

7. The method of claim 6, further comprising:
receiving input regarding at least one supplemental factor selected from (a) supplemental treatment received by the user, (b) user physical activity, and (c) mood polling of the user; and
determining and communicating visible-light exposure targets to the user based, in part, on the supplemental factor.

8. The method of claim 1, further comprising recording current time of day as the visible-light exposure from the light source is recorded.

9. The method of claim 8, further comprising modifying the recorded visible-light exposure received from the light source as a function of the recorded time of day associated with recorded visible-light exposure.

10. The method of claim 8, wherein visible-light exposure received in the evening is factored differently from visible-light exposure received during daytime hours.

11. The method of claim 1, further comprising providing an indication of an instantaneous visible-light exposure value in comparison with an established instantaneous visible-light exposure target.

12. The method of claim 11, wherein the established instantaneous visible-light exposure target is in a range from 2,500 to 10,000 lux.

13. The method of claim 1, wherein the light monitor also communicates visible-light exposure data to a remote person allowing the person to remotely monitor the user's visible-light exposure.

14. The method of claim 1, wherein the integrated light monitor also communicates visible-light exposure data to people known to the user.

15. The method of claim 1, wherein the active and direct feedback is communicated to the user via the mobile device.

16. The method of claim 15, where the mobile device is a smart phone.

17. The method of claim 1, wherein the feedback is provided in at least one of the following forms: an audible signal, vibration, text, and an application display indication.

18. A method for monitoring visible-light exposure, comprising:
positioning a light monitor including a visible-light detector and at least one of (a) an output device for indicating exposure to visible light and (b) a communication device;
receiving and recording visible-light exposure received from at least one light source with the visible-light detector of the light monitor;
either (i) integrating the recorded visible-light exposure from each light source or (ii) measuring instantaneous visible-light exposure to produce a visible-light exposure value;
comparing the visible-light exposure value with an established visible-light exposure target for a user to achieve a health benefit; and
providing active and direct feedback from at least one of:
(a) the output device and
(b) a smart device in communication with the communication device to the user, wherein the feedback is indicative of the visible-light exposure value in comparison with the established visible-light exposure target to empower the user to change behavior to achieve the benefit that is a consequence of reaching the visible-light exposure target.

* * * * *